US010307266B2

(12) United States Patent
Neubardt

(10) Patent No.: US 10,307,266 B2
(45) Date of Patent: Jun. 4, 2019

(54) HARVESTING BONE GRAFT MATERIAL FOR USE IN SPINAL AND OTHER FUSION SURGERIES

(71) Applicant: Seth L. Neubardt, Rye, NY (US)

(72) Inventor: Seth L. Neubardt, Rye, NY (US)

(*) Notice: Subject to any disclaimer, the term of this patent is extended or adjusted under 35 U.S.C. 154(b) by 263 days.

(21) Appl. No.: 15/583,490

(22) Filed: May 1, 2017

(65) Prior Publication Data
US 2017/0231784 A1    Aug. 17, 2017

Related U.S. Application Data

(60) Division of application No. 14/688,544, filed on Apr. 16, 2015, now Pat. No. 9,636,232, which is a continuation-in-part of application No. 14/524,044, filed on Oct. 27, 2014, now Pat. No. 9,833,332.

(51) Int. Cl.
A61B 17/16    (2006.01)
A61F 2/46    (2006.01)
A61F 2/44    (2006.01)
A61B 17/32    (2006.01)
A61F 2/30    (2006.01)

(52) U.S. Cl.
CPC ........ A61F 2/4601 (2013.01); A61B 17/1635 (2013.01); A61B 17/1671 (2013.01); A61B 17/320068 (2013.01); A61F 2/442 (2013.01); A61F 2/4455 (2013.01); A61F 2/4611 (2013.01); A61F 2/4644 (2013.01); A61B 2017/320072 (2013.01); A61F 2002/30471 (2013.01); A61F 2002/30845 (2013.01); A61F 2002/445 (2013.01); A61F 2002/4648 (2013.01); A61F 2002/4649 (2013.01)

(58) Field of Classification Search
CPC ............ A61B 17/1635; A61B 17/1671; A61F 2002/445
See application file for complete search history.

(56) References Cited

U.S. PATENT DOCUMENTS

| 7,201,775 | B2 | 4/2007 | Gorensek et al. |
| 7,618,423 | B1 | 11/2009 | Valentine et al. |
| 8,328,870 | B2 | 12/2012 | Patel et al. |
| 8,343,178 | B2 | 1/2013 | Novak et al. |
| 8,353,912 | B2 | 1/2013 | Darian et al. |
| 9,042,960 | B2 | 5/2015 | Neubardt |
| 2004/0230305 | A1* | 11/2004 | Gorensek ................ A61F 2/446 623/17.11 |
| 2011/0196373 | A1* | 8/2011 | Jacob ................ A61B 17/1671 606/79 |

* cited by examiner

*Primary Examiner* — Samuel S Hanna
(74) *Attorney, Agent, or Firm* — Leo Zucker

(57) ABSTRACT

A procedure for harvesting graft material for use during bone fusion surgery. A generally U-shaped cutting blade is inserted to a certain position inside a defined space between adjacent bones to be fused, and the cutting blade is rotated so that it cuts into the adjacent bones and forms a solid bone segment within each one of the bones. Each bone segment is displaced so that a first end portion of the segment enters the bone opposite the bone within which the segment was formed, an intermediate portion of the segment spans the space between the bones, and a second end portion of the segment remains in the bone within which the segment was formed. Each bone segment thereby acts as a strut graft for promoting a fusion of the adjacent bones to one another.

15 Claims, 10 Drawing Sheets

HARVESTING BONE GRAFT MATERIAL FOR USE IN SPINAL AND OTHER FUSION SURGERIES

CROSS REFERENCE TO RELATED APPLICATIONS

This application is a divisional of my co-pending U.S. patent application Ser. No. 14/688,544 filed Apr. 16, 2015, which is a continuation-in-part of U.S. patent application Ser. No. 14/524,044 filed Oct. 27, 2014.

BACKGROUND OF THE INVENTION

Field of the Invention

The present invention relates to a procedure for harvesting bone graft material for use in bone fusion surgery, including but not limited to fusions of the spine.

Discussion of the Known Art

An object of spinal fusion surgery is to join vertebrae at an affected level of a patient's spine, by inducing the growth of bone tissue that is deposited between the vertebrae during surgery. When fully grown, the deposited bone tissue fuses the vertebrae solidly and permanently. The procedure is long known to reduce or eliminate severe back pain when, for example, an intervertebral disc is damaged or becomes ineffective. See, e.g., U.S. Pat. No. 9,042,960 (May 26, 2015) which is incorporated herein by reference.

In a typical fusion procedure, the disc space between the vertebrae is cleaned, and bone or a bone g raft material is deposited in the space in a way that allows the material to grow and achieve a healthy fusion. Among available bone graft materials, graft harvested directly from the patient's own bone tissue (autograft) or from a donor, ceramics, bone morphogenic proteins, and/or stem cell based grafts are frequently used. Of these, autograft obtained from the patient's iliac crest or pelvic area is known to work best to achieve a successful fusion.

Using the patient's own bone tissue as graft material works well to form a confluence of the material with the vertebral bones to be fused. It is also known that (a) the more autograft material used, the greater the likelihood of achieving a successful fusion, and (b) a solid piece of autograft material works better than smaller chips to promote fusion. Basic principles of orthopaedic surgery suggest that an optimum fusion results when a solid piece of bone is inserted to span the entire intervertebral disc space, and when opposite ends of the piece enter or penetrate the vertebral end plates facing the space.

U.S. Pat. No. 7,201,775 (Apr. 10, 2007), incorporated by reference, discloses a procedure that includes implanting a hollow cylindrical stabilizing device (see FIGS. 7 & 8 of the patent) between the end plates the vertebrae to be fused, and rotating the device so it gouges and shears off portions of the end plates which portions are then forced inside the device. The device has openings so that when oriented as in FIG. 11C of the patent, the sheared bone portions are exposed to the vertebrae through openings in the device in order to promote fusion. The procedure does involve a risk of crushing the end plates and thus destroying the integrity of the remaining vertebral bone, however. That is, after the end plates are sheared by the device, one or both vertebrae may become prone to fracture and compress into the spinal canal. Also, the device does not work to translocate or displace a solid piece of bone from one vertebra so that an end of the piece enters the body of the other vertebra.

U.S. Pat. No. 8,328,870 (Dec. 11, 2012) describes an interbody fixation system including a cage having a number of blades mounted inside the cage. According to the patent, when the blades are turned not more than 45 degrees as shown in FIGS. 2 and 6C of the patent, the blades bite into the end plates of the opposed vertebrae and fix the position of the cage on and between the end plates.

See also U.S. Pat. No. 7,618,423 (Nov. 17, 2009) which relates to a system for performing spinal fusion including a graft holder assembly, a locking assembly, and a pair of bone graft implants that are introduced into a disc space to effect fusion; U.S. Pat. No. 8,353,912 (Jan. 15, 2013) disclosing an ultrasonic cleaning device for leveling the surfaces of vertebral end plates after the disc space between them is cleaned and before graft material is deposited in the space; U.S. Pat. No. 8,343,178 (Jan. 1, 2013) describing an ultrasonic saw blade for cutting hard bone without damaging adjacent soft tissue; and U.S. Patent Application Pub. No. 2011/ 0196373 (Aug. 11, 2011) disclosing a bone preparation device having a cutter component for shaping the endplates of adjacent vertebrae to mate closely with an intervertebral implant. All of the foregoing patent documents are incorporated by reference.

Notwithstanding the known meticulous procedures for obtaining and using autograft material from a patient during surgery, there is no guarantee that a reliable and strong fusion will always be obtained, or that a so-called "nonunion" will not occur. A need therefore exists for a system and procedure for obtaining autograft material from a patient during a bone fusion surgery, and for depositing the material between the bones to be fused so that (a) the material spans the space between the bones and also enters the bones, and (b) the material grows rapidly to obtain a healthy, strong, and permanent fusion of the bones.

SUMMARY OF THE INVENTION

According to the invention, a procedure for harvesting graft material for use during bone fusion surgery includes inserting a generally U-shaped cutting blade to a certain position inside a defined space between adjacent bones to be fused, and rotating the cutting blade so that it cuts into the adjacent bones and forms a solid bone segment within each one of the bones. Each bone segment is displaced so that a first end portion of the segment enters the bone opposite the bone within which the segment was formed, an intermediate portion of the segment spans the space between the bones, and a second end portion of the segment remains in the bone within which the segment was formed. Each bone segment thus acts as a strut graft to promote fusion of the adjacent bones to one another.

According to another aspect of the invention, a procedure for harvesting graft material for bone fusion surgery includes forming a generally U-shaped cutting blade to extend from a distal end of an elongated tool shaft having an axis, inserting the cutting blade at the end of the tool shaft to a desired position in a defined space between the bones, and rotating the tool shaft about its axis so that the cutting blade cuts into the bones to form corresponding solid bone segments.

A paddle is configured to extend from a distal end of a cannulated paddle shaft, and the paddle shaft is slid over the tool shaft until the paddle confronts exposed surfaces of the solid bone segments formed by the cutting blade at the distal end of the tool shaft. The paddle shaft is rotated so that the paddle at the distal end of the paddle shaft urges the bone segments to a position where a leading portion of each segment enters the bone opposite the bone from which the segment was formed, a central portion of the segment spans the space between the bones, and a trailing portion of the segment remains inside the bone from which the segment was formed, whereby the bone segments define strut grafts for fusing the bones to one another.

According to a further aspect of the invention, a procedure for harvesting graft material for bone fusion surgery includes providing a cage having a front wall, a rear wall, and a chamber inside the cage between the front and the rear wall. A bone cutting mechanism including a generally U-shaped cutting blade and a paddle is arranged within the chamber between the front and the rear wall of the cage. The cutting blade has a base, a pair of legs spaced apart a certain width from one another, and a closed end that extends a certain length from the base of the blade, and both of the cutting blade and the paddle are rotatable about a common axis.

The cage is inserted to a desired position in a defined space between adjacent bones that are to be fused to one another, and the cutting blade is rotated so that the blade cuts into the bones and forms a generally semicircular solid bone segment within each one of the bones. Each bone segment thus has a width corresponding to the spacing between the legs of the cutting blade, and a radius corresponding to the length between the base and the closed end of the cutting blade.

The paddle is rotated to displace the solid bone segments formed within the adjacent bones angularly, so that a first end portion of each bone segment enters the bone opposite the bone within which the segment was formed, an intermediate portion of the bone segment spans the space between the bones, and a second end portion of the bone segment remains in the bone within which the segment was formed. Accordingly, each bone segment thus defines a strut graft for promoting a fusion of the adjacent bones to one another.

For a better understanding of the invention, reference is made to the following description taken in conjunction with the accompanying drawing and the appended claims.

BRIEF DESCRIPTION OF THE DRAWING FIGURES

Figure 1:
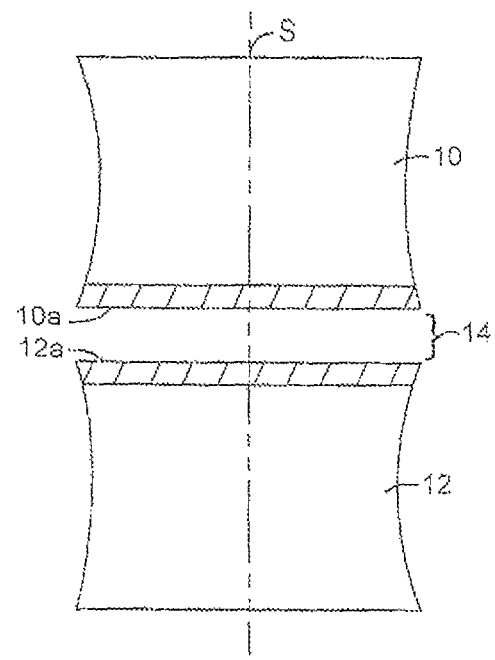
FIG. 1 illustrates two adjacent spinal vertebrae to be fused to one another, according to a first embodiment of the invention.
Figure 6:
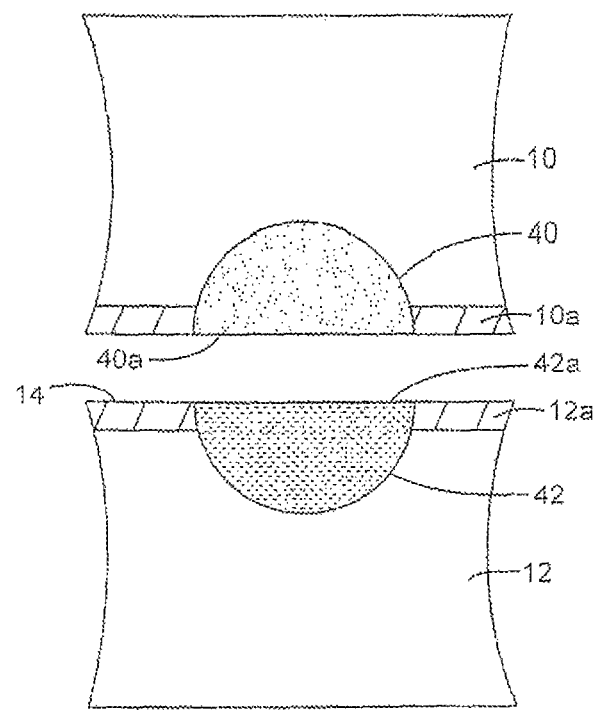
FIG. 6 illustrates two bone segments that are cut and formed inside the vertebrae by the tool blade.
Figure 10:
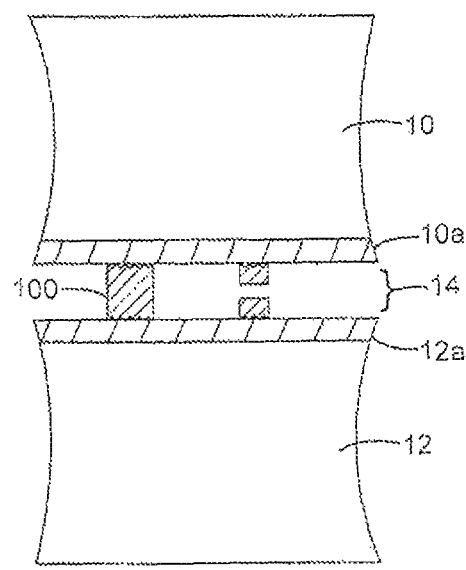
Figure 8:
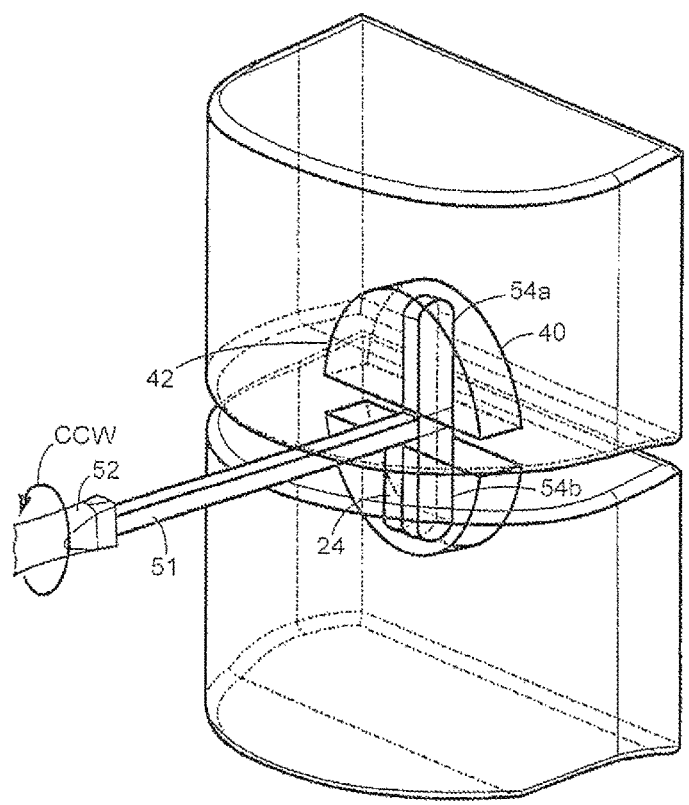
FIG. 8 is a view similar to FIG. 7, showing the paddle inserted in the disc space and after turning 90 degrees from the position in FIG. 7.
Figure 9:
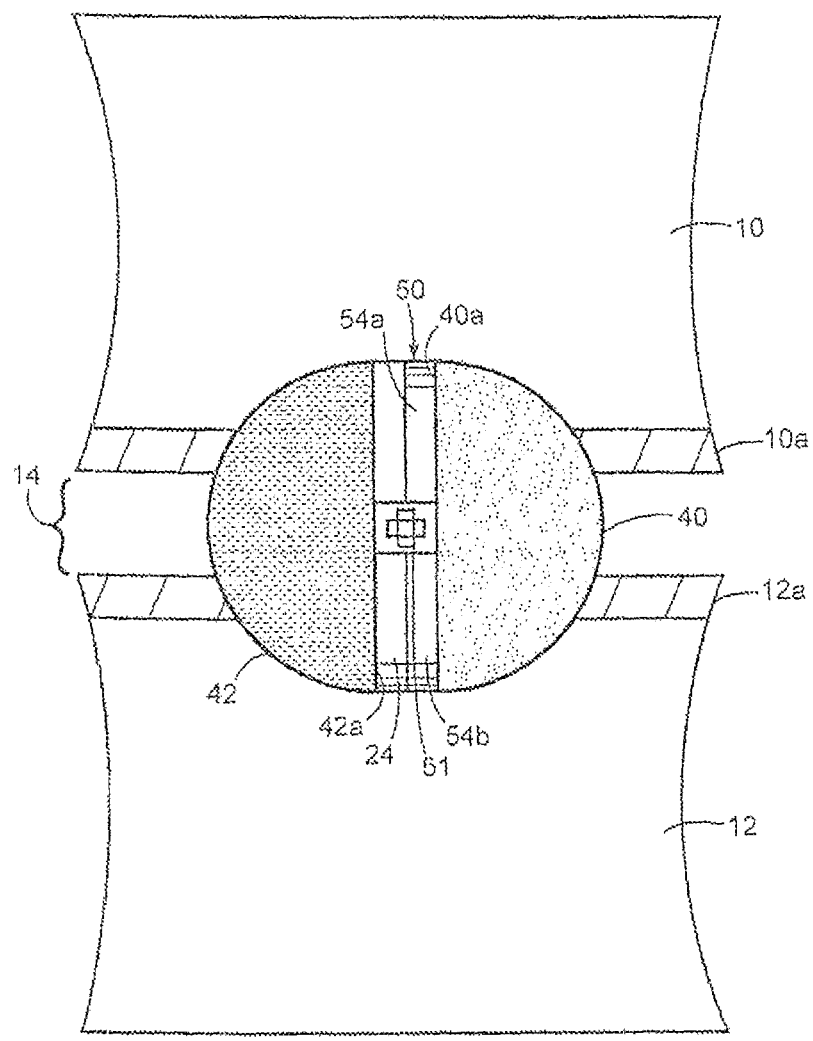
Figure 11:
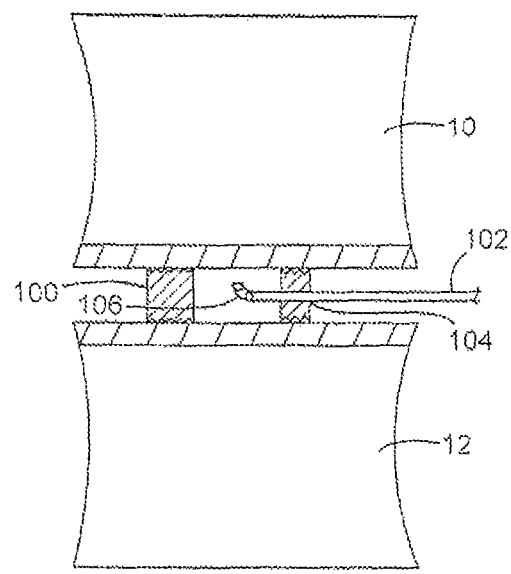
Figure 12:
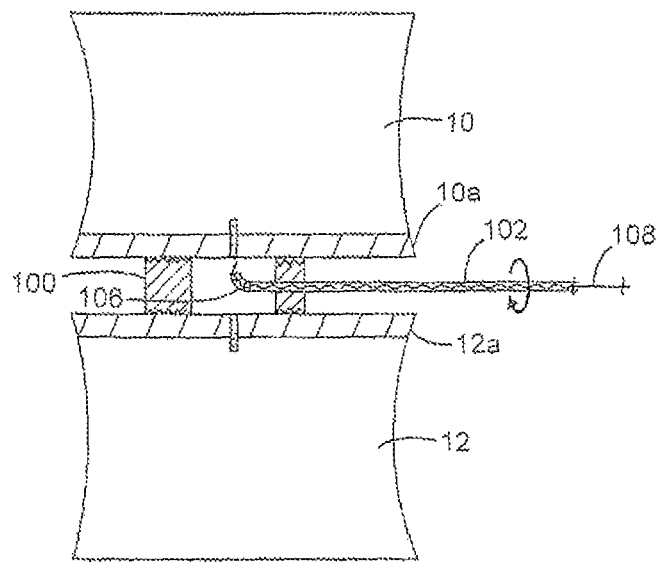
Figure 13:
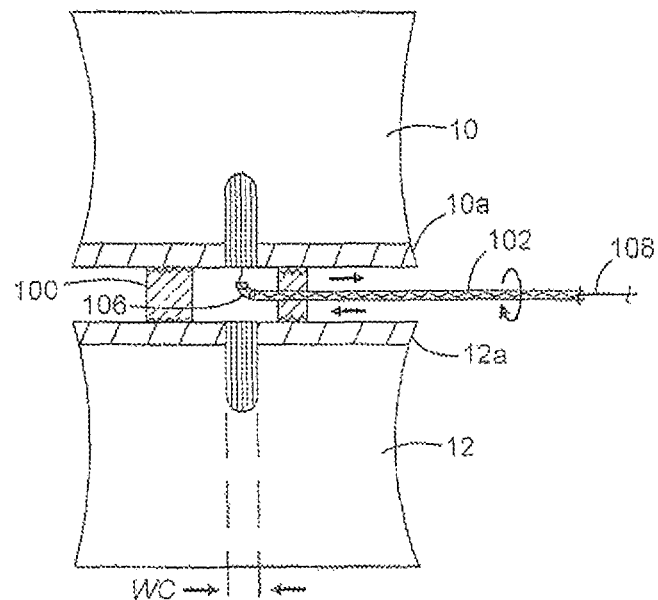
Figure 14:
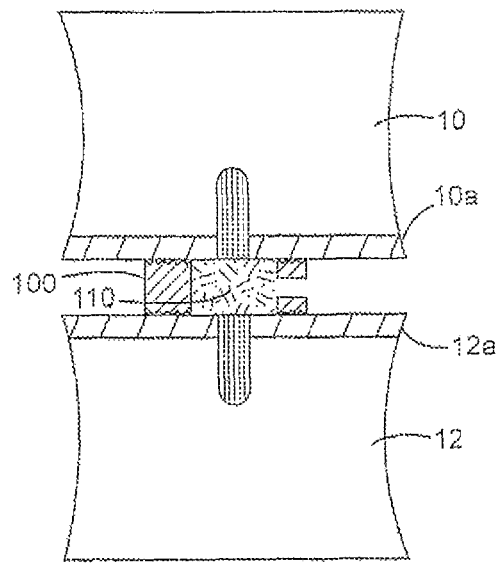
Figure 15:
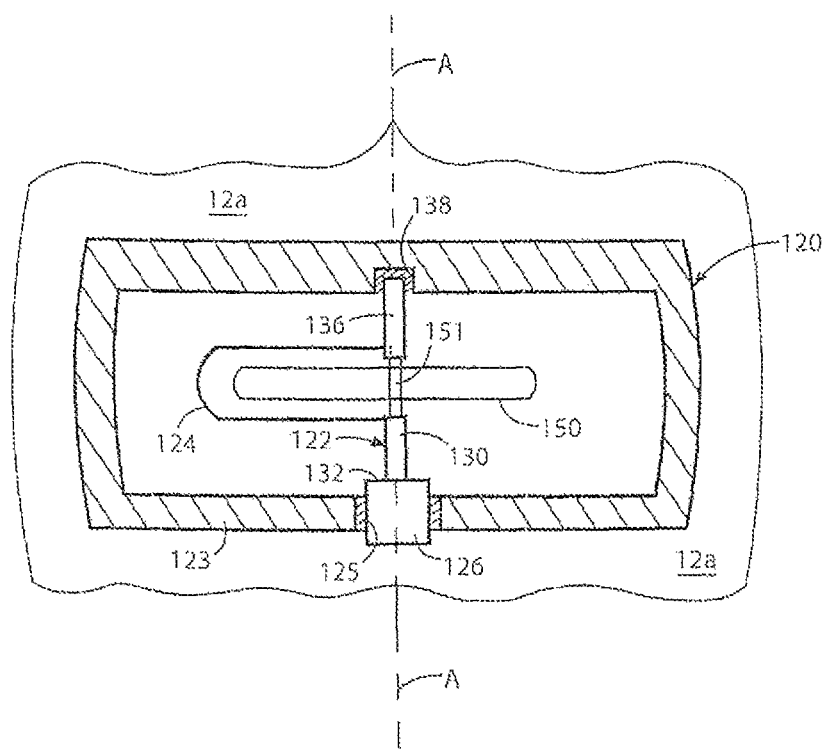
Figure 16:
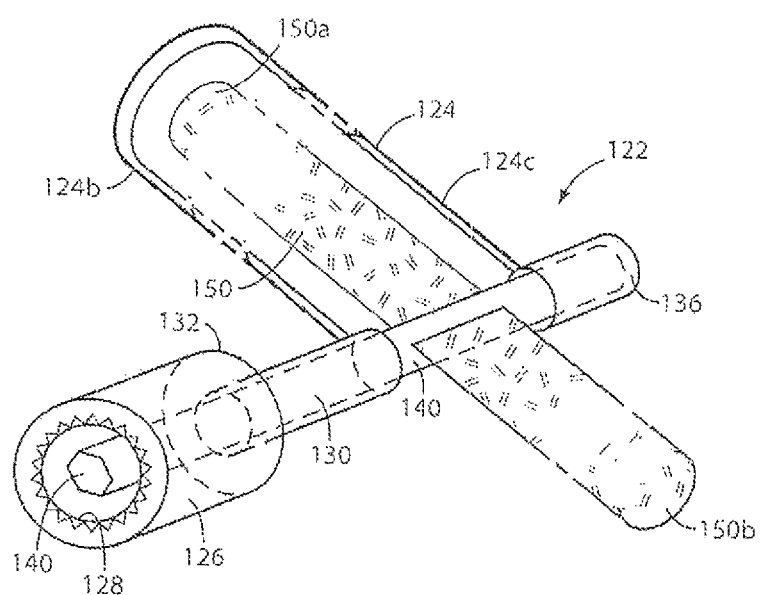

FIG. 9 shoes the bone segments in FIG. 6 acting as strut grafts between the vertebrae when the paddle is in the position in FIG. 8, according to the invention:

FIG. 10 shows the vertebrae in FIG. 1 before fusion and with a cage inserted in the disc space, according to a second embodiment of the invention;

FIG. 11 shows a distal end of a cannula inserted in the disc space through an opening in a side wall of the cage in FIG. 10;

FIG. 12 shows a cutting tip of a flexible wire inserted through the cannula and into the disc space, with the wire tip angled toward one of the vertebrae;

FIG. 13 shows the tip of the wire cutting multiple grooves in the vertebrae to be fused;

FIG. 14 depicts the effusion of a bony slurry from the cut vertebrae, and the confinement of the slurry in the cage, according to the invention;

FIG. 15 shows the interior of a cage including a bone cutting blade and paddle mechanism fixed inside the cage, according to the invention; and FIG. 16 is an enlarged view of the blade and paddle mechanism in FIG. 15.

DETAILED DESCRIPTION OF THE INVENTION

The present invention concerns a procedure for harvesting bone graft material from a patient during bone fusion surgery. The illustrated embodiments are directed to spinal fusion surgeries in which adjacent vertebrae are prepared to be fused to one another, and the harvested bone graft material spans the disc space between the vertebrae and also enters the vertebral bodies. As a result, the graft material grows quickly and obtains a healthy, solid, and permanent fusion. While the invention is illustrated and described herein in terms of spinal fusion surgery, persons skilled in the art will recognize that the invention can also be applied to other fusion surgeries, for example, fusions of the ankle bones.

FIG. 1 is a diagram of two adjacent spinal vertebrae 10, 12. The spine has an axis S, and the vertebrae 10, 12 are separated by a disc space 14. End plates 10a, 12a on the vertebrae face one another across the disc space 14.

Figure 2:
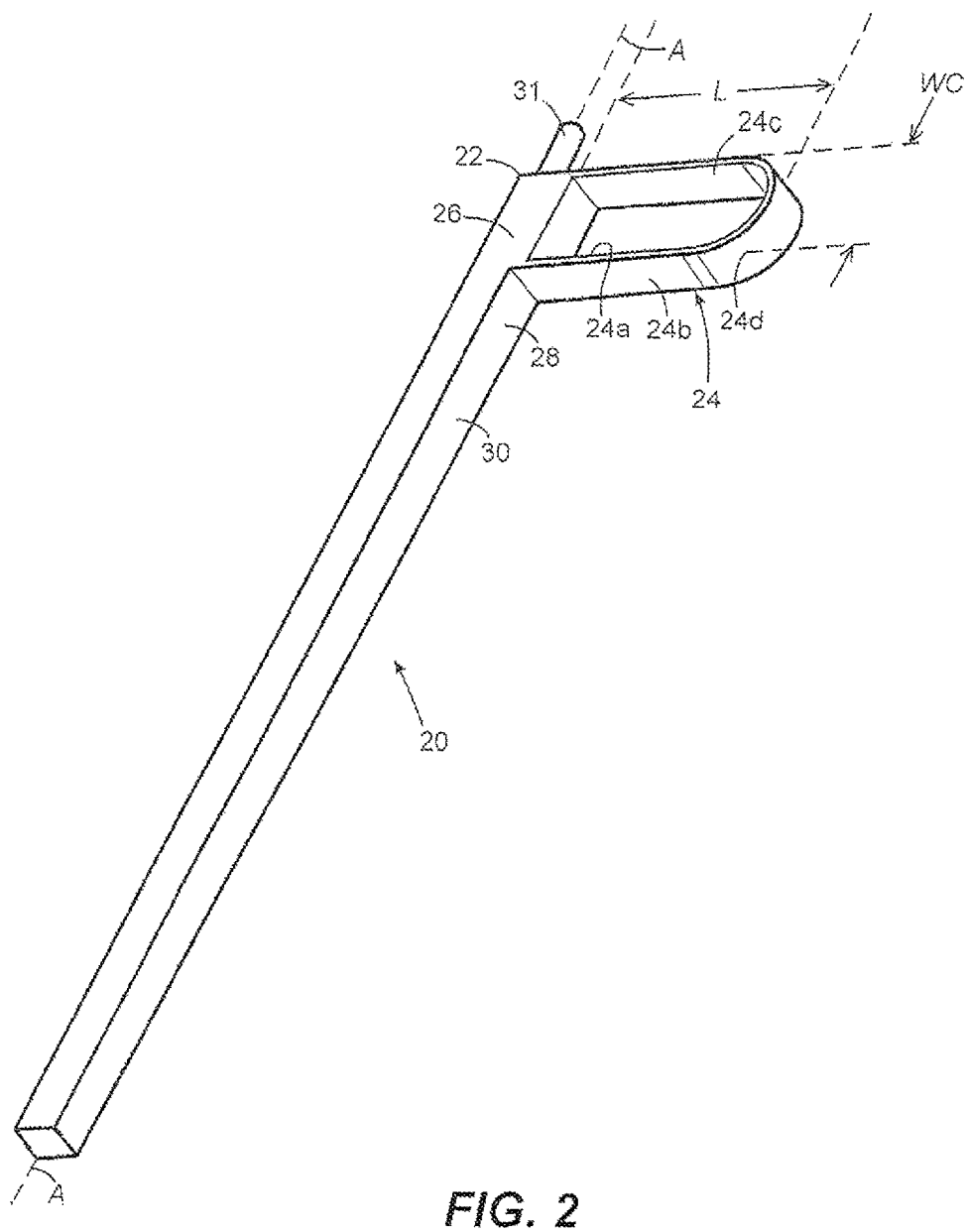
FIG. 2 shows a bone cutting tool having a shaft and a cutting blade at a distal end of the shaft, according to the invention.

In one embodiment of the invention, shown in FIGS. 2 to 9, a bone cutting tool 20 has a shaft 30 with a long axis A, and a generally U-shaped, ultrasonic cutting blade 24. The blade 24 has a base 26, and a cutting edge 24a formed along parallel legs 24b, 24c and a closed end 24d of the U shaped blade 24. As shown in FIG. 2, the blade legs 24b, 24c are spaced apart by width WC, and the closed end 24d of the blade extends radially by a length L from the base 26.

Figure 3:
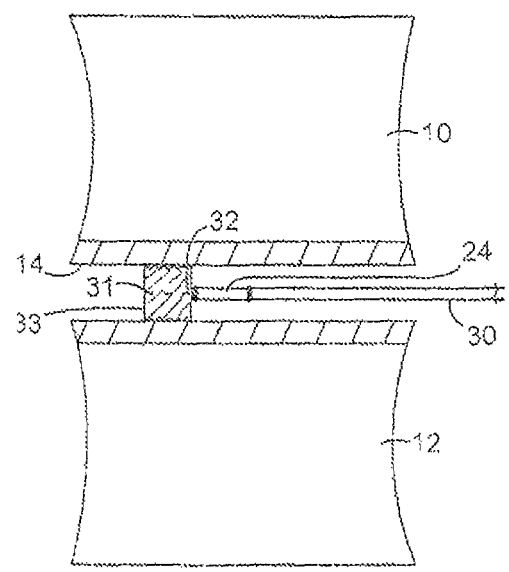
FIG. 3 shows the tool shaft in FIG. 2 inserted in a disc space between the vertebrae in FIG. 1, and a cage on which the shaft is pivoted to rotate with the blade.

The blade base 26 is formed by a distal end 28 of the tool shaft 30, and a pivot 31 projects axially from the distal end of the shaft. As seen in FIG. 3, the pivot 31 is received in a corresponding pivot opening 32 that is formed in a spacer or cage 33, after the cage 33 is fixed at a desired position in the disc space 14 between the vertebrae 10, 12. The cage 33 may be formed of a surgical metal, a polymer, a ceramic, or composites thereof. The pivot opening 32 in the cage 33 acts as an anchor point for the tool shaft 30 and any other instrumentation to be inserted in the disc space 14 while the cage 33 supports the vertebral bones 10, 12 above and below the disc space, thereby preventing subsidence of bone graft segments to be obtained as described below. The cage 33 also serves to enhance the stability of the entire construct and thus ensures a successful fusion.

If surgery is performed using a posterior approach, the cage 33 is inserted in the disc space 14 from the posterior side, and should be urged anteriorly as far as possible to lodge against the disc annulus as the vertebral bones 10, 12 compress the cage 33 from above and below. To provide an effective anchor point for the pivot 31 on the tool shaft 30, the cage 33 should be relatively large and curvilinear in shape to conform with the anterior disc space occupied by the cage. Cages typically have one or more apertures to allow bone graft material to be deposited inside them, and for the material to be exposed to and contact the vertebrae above and below the cage to allow the material to grow and bond the vertebrae 10, 12 solidly to one another.

Because, according to the invention, bone graft material is obtained directly from the vertebrae to be fused instead of from an outside source, it is therefore not necessary for the cage 33 to act primarily as a fusion device. Rather, the cage 33 can work mainly as a fixation device that joins to the vertebral bones 10, 12 above and below. An existing cage that also serves as a fixation device is available from Biomet, Inc., as the C-THRU™ Anterior Spinal System.

The above cage from Biomet has a large chamber that opens at top and bottom (superior and inferior) ends of the cage, and graft material can be packed inside of the chamber. Although as shown in FIG. 3 the cage 33 is not directly centered with respect to the end plates 10a, 12a of the vertebrae to be fused as described below, it may be desirable to use a cage similar to Biomet with a chamber that opens at both ends, and to form an opening in a side wall of the cage so that the blade 24 can be inserted by the tool shaft 30 inside the cage chamber. In such a case, the cage 33 may be centered on the vertebral end plates 10a, 12a before the blade 24 cuts into the end plates 10a, 12a as described below.

Figure 4:
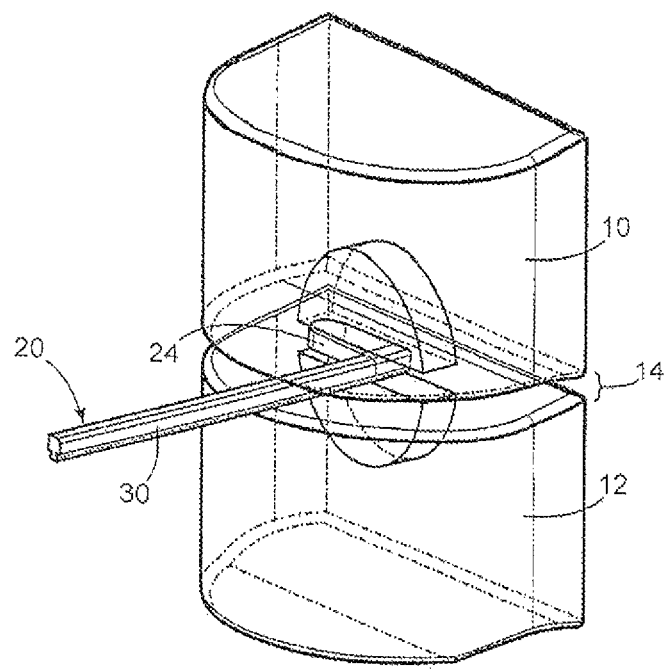
FIG. 4 is an enlarged, isometric view of the tool shaft and the blade inserted in the disc space as in FIG. 3.
Figure 5:
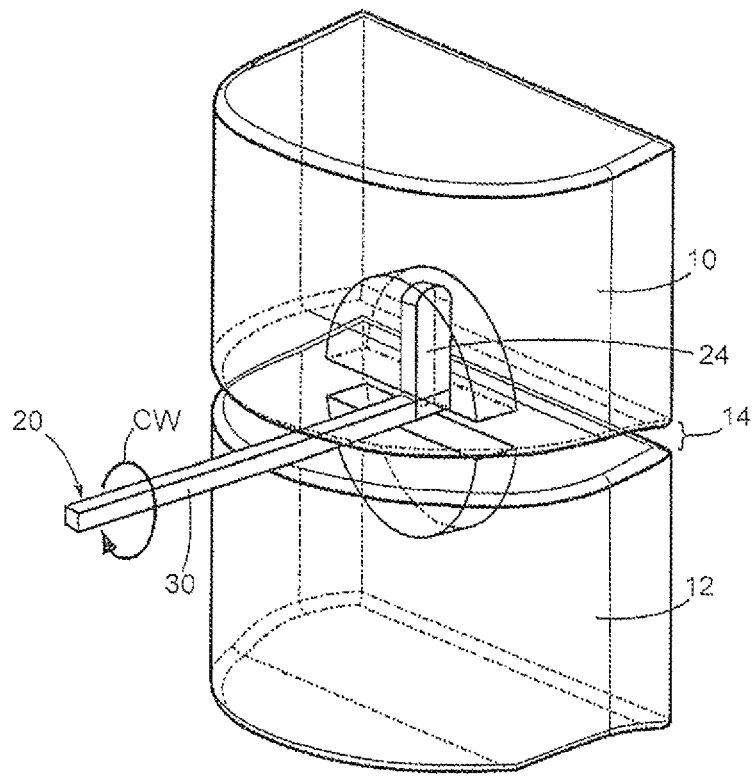
FIG. 5 is a view similar to FIG. 4, after the blade is turned 90 degrees from the position in FIG. 4 by the tool shaft.

As seen in FIG. 2, the U shaped blade 24 extends radially outward from its base 26 at the distal end 28 of the tool shaft 30. The legs 24b, 24c, and the closed end 24d of the blade 24 are in a plane that contains the shaft axis A. The bone cutting tool 20 with the blade 24 is dimensioned and formed so that the blade 24 can be inserted by the tool shaft 30 to a desired position in the disc space 14, with the plane of the blade 24 kept generally parallel to the end plates 10a, 12a of the vertebrae to be fused, as shown in FIG. 4. The cutting edge 24a along the blade 24 is activated, for example, by a conventional ultrasonic driver coupled in a known manner to the tool shaft 30. Ultrasonic bone cutting blades and methods of activating them are generally known, and persons skilled in the art will be able to construct and use the blade 24 as described herein. See, www.misonix.com.

The tool shaft 30 is rotated about its axis A by, e.g., a removable or cannulated handle having an axial thru passage keyed to the shaft cross section, or by a flexible motor drive, so that the blade's cutting edge 24a is urged a over a circular path through the vertebral end plates 10a, 12a, and adjacent regions inside the vertebrae 10, 12. See FIG. 5. As a result, and as illustrated in FIG. 6, the blade 24 forms two semi-circular solid bone segments 40, 42 in the vertebral bodies 10, 12 such that the radius of each segment 40, 42 corresponds to the radial length L of the blade 24, and the thickness of each segment corresponds to the spacing WC of the parallel blade legs 24b, 24c.

The bone segments 40, 42 are then used as autologous graft material which, as explained below, will form strut grafts between the same vertebrae 10, 12 from which the segments are cut. Note in FIG. 6 that after the segments are formed by the blade 24, relatively flat surfaces 40a, 42a on the segments are exposed to face one another across the intervertebral disc space 14. While the cutting blade 24 can be withdrawn from the disc space 14 together with the tool shaft 30 at this time, it may be desirable to leave the blade 24 and the shaft 30 in place, as noted below.

Figure 7:
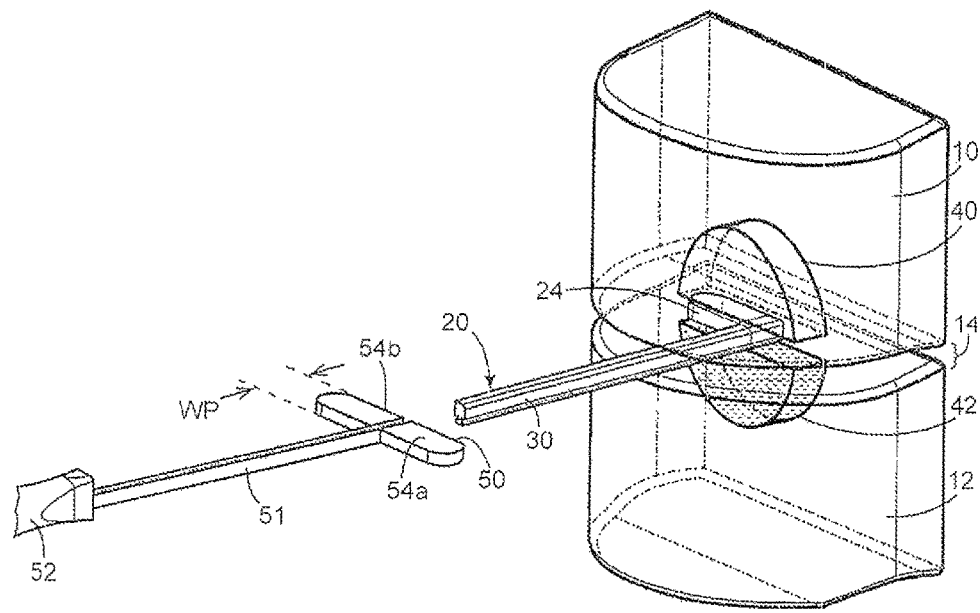
FIG. 7 is an isometric view of a pusher or paddle at a distal end of a shaft.

After removing a handle or other drive from the tool shaft 30, and as shown in FIGS. 7 to 9, an elongated pusher or paddle 50 is inserted into the disc space 14 until the paddle 50 is aligned with the blade 24 and the exposed surfaces of the bone segments 40, 42. In the illustrated embodiment, the paddle 50 is fixed at a distal end of a cannulated shaft 51 having an axial passage keyed to the cross section of the tool shaft 30. The cannulated shaft 51 is slid onto the tool shaft 30, a handle 52 is provided on the proximal end of the shaft 51, and the paddle 50 is inserted via the shaft 51 into the disc space 14. Using the handle 52, the paddle 50, together with the cutting blade 24 if left in place, is rotated about 90 degrees over the same circular path traversed by the blade 24 when forming the bone segments 40, 42, as described below.

Note that if the cage 33 in FIG. 3 is of such size as to encompass areas of the vertebral end plates 10a, 12a to be cut by the blade 24, then both the blade 24 and paddle 50 should be able to be inserted inside the cage and to operate within the bounds of the cage. See, e.g., the cage 120 in the embodiment of FIGS. 15 and 16. In such a case, the cage 33 may be formed with passages in its anterior and posterior facing side walls, so that the passages allow the cutting blade 24, paddle 50, and other required instrumentation to enter the cage from either direction depending on the approach taken by the surgeon.

In the illustrated embodiment, the paddle 50 includes two U-shaped paddle arms 54a, 54b that extend radially from the shaft 51 and 180 degrees apart from one another. See FIGS. 7 to 9. Each paddle arm 54a, 54b has a width WP that does not exceed the width WC of the bone cutting blade 24. Likewise, the length of each paddle arm 50a, 50b does not exceed about one-half the length of either of the bone segment surfaces 40a or 42a facing the disc space 14. The entire paddle 50 may also be formed from one or more balloons which, when inflated, take the form of a rigid pusher or paddle device.

When the paddle 50 is inserted in the disc space 14, the paddle arms 54a, 54b are generally parallel to and overlie the surfaces 40a, 40b of the bone segments. The cannulated shaft 51 is turned about its axis A so that the paddle arms urge the bone segments 40, 42 confronting the arms to rotate partially out of the vertebra from which the segment was cut by, e.g., about 90 degrees as in FIG. 9. Accordingly, (i) a leading portion of each segment 40, 42 enters the vertebra opposite the vertebra from which the segment was formed, (ii) a central portion of each segment spans the disc space 14, and (iii) a trailing portion of each segment remains inside the vertebra from which the segment was formed.

When rotated as described above and shown in FIG. 9, each one of the bone segments 40, 42 forms a vertical strut graft that spans the disc space 14 fully and also penetrates both of the vertebrae 10, 12 to be fused. Each strut graft will therefore act as a pathway for bone growth and promote a healthy fusion of the two vertebrae. The tool shaft 30 may be withdrawn from the cage 33 inside the disc space 14, and the paddle 50 and the cutting blade 24 can remain in a vertical position sandwiched between the strut grafts formed by the bone segments with no adverse affect on the quality of the ensuing fusion.

After the blade 24 cuts into the vertebrae and the formed bone segments 40, 42 are rotated by the paddle 50, a massive release of blood will likely occur because the bone is very vascular. Accordingly, in addition to inserting and using a cage similar to the mentioned Biomet device in the disc space 14, a system should be in place to extinguish such hemorrhaging. One approach is to use a coagulating agent such as, for example, the Surgiflo® Hemostatic Matrix available from Ethicon US, LLC, and injecting the agent through an applicator tube into a port formed on the cage 33. Also, with much bleeding, there may be a need to seal the disc space 14 so the coagulating agent will stay inside the space. That is, the disc space 14 may need to be capped or sealed closed to confine the blood, the coagulating agent, and the graft bone segments inside the disc space. Once the coagulating agent is injected in the closed disc space, a pressurized environment is created and the bleeding should stop.

The cage may also have ports situated so that the coagulating agent produces a seal between the upper and the lower surfaces of the cage, and the adjacent vertebral bone. The seal should help to prevent bloody fluid from escaping above and below the cage through small gaps.

As the paddle 50 turns, and as described above, the paddle arms 54a, 54b are urged against the confronting surfaces 40a, 42a of the bone segments 40, 42 after the segments are cut and formed by the blade 24. The paddle 50 therefore does not occupy any space in which new bone graft will be deposited. Thus, as noted above, the paddle 50 can remain in the position in FIG. 9 with the graft bone segments 40, 42 at each side, and the vertebral bones 10, 12 above and below the paddle. Moreover, as the bones 10, 12 heal and the graft bone segments 40, 42 grow, the paddle 50 becomes firmly anchored inside the vertebrae 10, 12 and adds stability to the overall construct by pinning the vertebrae together. To that end, the paddle 50 may be constructed, for example, with extensible pins to engage the confronting surfaces 40a, 42a of the bone segments and/or the vertebrae 10, 12 above and below the paddle 50. Such engagement would stabilize the construct and ensure that the paddle 50 and the graft bone segments 40, 42 do not migrate. Together with the cage 33, the paddle 50 will also prevent subsidence from a collapse of the disc height.

It is also possible for the paddle 50 to be formed as a balloon so that, if desired after inflation and use, the paddle can be deflated and easily removed after being turned to the position in FIG. 9 along with the bone segments 40, 42 at either side. In such a scenario, any additional fixation that would otherwise result by using a more solid form of the paddle 50 would not be realized unless the balloons are later filled with a material such as, e.g., methyl methacrylate that would harden the balloons in place.

The paddle 50 may also be constructed in a known manner so that the paddle arms 54a, 54b overlie one another at one side of the cannulated shaft 51 as the paddle 50 is inserted in the disc space 14. Once positioned between the bone segments 40, 42, one of the paddle arms may then be displaced to the opposite side of the shaft 51 so that the paddle arms overlie both of the confronting surfaces 40a, 42a on the bone segments.

It may also be preferable to allow the solid bone cutting blade 24 to remain in situ, and no attempt made to withdraw it from between the bone segments 40, 42 once the bone segments are formed and the paddle 50 enters the disk space 14. This would help to ensure that the paddle arms 54a, 54b will follow the same path previously cut by the blade 24 when forming the bone segments. A deviation of even a millimeter to either side of the path might cause the paddle arms 54a, 54b to lock or jam against solid uncut vertebral bone and prevent the arms from urging the segments 40, 42 fully toward the position in FIG. 9. If the dimensional tolerances of the cage 33 allow enough precision with respect to positioning the cutting blade 24 and the paddle 50 during use, then it may be possible for the blade 24 to be withdrawn before the paddle 50 is inserted and the paddle arms are deployed.

The inventive system therefore has the following desirable features:

1. The bone cutting blade 24 can be activated ultrasonically to make the vertebral cuts safely and precisely;
2. The blade 24 and the paddle 50 can be made small enough to be inserted in the intervertebral disc space 14 during a minimally invasive surgical procedure; and
3. In addition to adding stability to the construct, the cage 33 provides a common fixed pivot point about which the cutting blade 24 and the paddle 50 can rotate, thereby ensuring that the bone segments 40, 42 will turn smoothly and accurately within the vertebrae 10, 12 when urged to do so by the paddle.

Another embodiment of the inventive system is illustrated in FIGS. 10 to 14. Instead of cutting and forming the solid graft bone segments 40, 42 and displacing them angularly as described above, a bone cutting instrument having a straight rather than a two-dimensional or U shaped cutting edge like the blade 24 is inserted in the disc space 14. The instrument is operated to strike the vertebral bones 10, 12 and to groove them so that a slurry of morselized cortical and cancellous bone rich in osteogenic cells and blood oozes from the vertebrae. By confining the slurry inside the disc space 14, portions of the slurry also remain within the grooved portions of both vertebrae to produce a solid bony fusion.

A cage 100 is set in the disc space between the vertebrae 10, 12. See FIG. 10. The cage 100 may be similar to the earlier mentioned Biomet C-THRU Anterior Spinal System device, or equivalent. In addition, the cage 100 should have sufficient size and volume to contain and confine the slurry obtained from the vertebrae as detailed below, and be constructed so that its edges seal any gaps between the cage and either bone 10, 12. Such sealing prevents liquid graft material from migrating outside the internal chamber of the cage 100 and the intervertebral disc space. For example, a seal can be formed by constructing the cage 100 with internal and/or external channels that guide a sealing agent around the circumference of the superior and inferior edges of the cage 100, and the agent can be injected into the cage during the fusion procedure. The mentioned Surgiflo® Hemostatic Matrix is an example of such a sealing agent.

As seen in FIGS. 11 to 13, a cannula 102 is inserted through an opening 104 in the wall of the cage 100, and the cannula 102 has a distal tip 106 that is angled to be directed toward the vertebrae above and below the perimeter of the cage when the cannula 102 is rotated about its axis. A flexible, sharp tipped wire 108 is inserted through the cannula 102, past the distal tip 106 of the cannula, and against the end plate 10a or 12a of a confronting vertebra. A motor or other drive mechanism is coupled to a proximal end of the cannula 102, and spins the cannula over multiple revolutions so that the tip of the wire 108 cuts into the end plates 10a, 12a of both vertebrae.

The wire 108 is urged farther into the cannula 102 so that the wire tip cuts a groove completely through the end plates and adjacent regions of the vertebrae 10, 12, as seen in FIG. 12. The position of the wire 108 at the tip 106 of the cannula is adjusted and the cannula 102 is moved axially in anterior and posterior directions so that the combined width WC of all the vertebral cuts is increased as desired. See FIG. 13. The cannula 102 and wire 108 are then withdrawn from inside the cage 100 and the disc space.

As a result and as shown in FIG. 14, all of the bony slurry 110 obtained from the cut vertebrae is contained either inside the cage 100 in the disc space, or within the vertebrae 10, 12 in the region of the grooved cuts. Upon healing, the slurry forms a solid bony fusion of the vertebrae. If needed, a second cage or other device can be provided to cap or otherwise seal the cage 100 and the disc space to ensure the slurry stays so confined before healing.

FIG. 15 is a plan view of the interior of a cage 120 having a built-in blade and paddle mechanism 122 constructed and arranged to be operated from outside the cage 120, according to a further embodiment of the invention. FIG. 16 is an enlarged view of the blade and paddle mechanism 122.

The cage 120 may be formed, for example, from a surgically approved metal or metal alloy, or a strong plastics such as polyether ether ketone (PEEK). The side walls of the cage 120 as viewed in FIG. 15 are preferably as thin as possible while still having enough strength to prevent the cage 120 from deforming after the cage is inserted and fixed between spinal vertebrae or other bones to be fused.

A front wall 123 of the cage 120 in FIG. 15 has an opening 125 in which a head 126 of a first shaft 130 and a front end of a second shaft 140 (see FIG. 16), can each be accessed by a corresponding tool to rotate the associated shaft. That is, the shafts 130, 140 can be rotated independently of one another as desired by a mating tool from outside the cage 120. In the disclosed embodiment, the first shaft 130 is hollow, and the second shaft 140 extends coaxially inside the first shaft 130.

As shown in FIG. 16, the head 126 of the first (or outer) shaft 130 is, for example, in the form of a cylindrical socket having a series of teeth or grooves formed about its inner circumference for engaging a mating tool bit. The outer shaft 130 extends axially a certain distance from a rear wall 132 of head 126 toward a back wall of the cage 120, and a first leg 124*b* of a generally U-shaped bone cutting blade 124, which may be similar to the blade 24 in FIG. 2, is joined at one end of the leg 124*b* to the shaft 130. The second leg 124*c* of the blade 124 is joined to a front end of a sleeve 136 that is aligned axially with the outer shaft 130, and a rear end of the sleeve 136 is seated in the rear wall of the cage 120 at 138 (FIG. 15) for smooth rotation about the sleeve axis.

The second (or inner) shaft 140 of the blade and paddle mechanism 122 extends axially inside the outer shaft 130, and through the sleeve 136 toward the rear of the cage 120. The front end of the inner shaft 140 is keyed and is accessible within the cylindrical head 126 of the outer shaft 130 so that the front end of the shaft can be engaged for rotation by a mating tool bit. A section of the inner shaft 140 is exposed between the end of the outer shaft 130 to which the blade leg 124*b* is joined, and the front end of the sleeve 136 where the blade leg 124*c* is joined.

A paddle 150 has a pair of arms 150*a*, 150*b* that extend radially from either side of the exposed section of the inner shaft 140, and the arms are spaced 180 degrees apart from one another. The paddle arms 150*a*, 150*b* are dimensioned and arranged to displace solid bone segments that are formed inside the bones to be fused after the blade 124 is rotated to cut through the bones, to positions at which the bone segments span and enter the bones to be fused so as form strut grafts. The axial width and the radial length of the paddle arms 150*a*, 150*b* are such that when the U-shaped blade 124 is rotated by the outer shaft 130 over one full revolution while the paddle arms remain stationary, the blade 124 clears the perimeters of the paddle arms by at least 1 mm, and preferably by not more than 5 mm.

In use, and as in the first embodiment of the present invention, the blade 124 is activated and rotated 360 degrees by the outer shaft 130 so as to cut into the bones above and below the cage 120 and thus form two semicircular solid bone segments. After the segments are formed, the paddle arms 150*a*, 150*b* are displaced angularly about 90 degrees by the inner shaft 140. Each bone segment is thereby urged by a confronting paddle arm to rotate until (i) a leading portion of the segment enters the opposed bone, (ii) a central portion of the segment spans the space in which the cage 120 is fixed between the bones, and (iii) a trailing portion of the segment remains in the bone in which it was formed.

While the foregoing represents preferred embodiments of the invention, it will be understood by those skilled in the art that various modifications, adaptations, and additions may be made without departing from the spirit and scope of the invention.

For example, while the invention is described herein as applied to a spinal fusion, the invention may be adapted for other bone fusion procedures as well, for example, fusions of the ankle bones. Further, although a particular configuration is disclosed herein to enable the blade and the paddle shafts 130, 140 each to be rotated as desired from outside the cage 120, other equivalent configurations for rotating the blade 124 and the paddle 150 inside the cage may also be used. See, e.g., U.S. Pat. No. 7,972,364 (Jul. 5, 2011) which is incorporated by reference.

Accordingly, the invention includes all such modifications, adaptations, and additions as are within the scope of the following claims.

I claim:

1. A procedure for harvesting graft material for use during bone fusion surgery, comprising:
    inserting a generally U-shaped cutting blade to a certain position inside a defined space between adjacent bones to be fused, wherein the cutting blade has a base, a pair of legs spaced apart a certain width from one another, and a closed end that extends a certain length from the base of the blade;
    rotating the cutting blade so that it cuts into the adjacent bones and forms a generally semicircular solid bone segment within each one of the bones, wherein each bone segment has a width corresponding to the spacing between the legs of the cutting blade, and a radius corresponding to the length between the base and the closed end of the cutting blade;
    displacing each solid bone segment angularly so that a first end portion of the segment enters the bone opposite the bone within which the segment was formed, an intermediate portion of the segment spans the space between the bones, and a second end portion of the segment remains in the bone within which the segment was formed;
    whereby each bone segment defines a strut graft for promoting a fusion of the adjacent bones to one another; and
    inserting a paddle into the defined space between the adjacent bones, and performing the displacing step by rotating the paddle.

2. The procedure of claim 1, wherein the adjacent bones to be fused are vertebrae in a patient's spine, and the defined space inside of which the cutting blade is inserted is a disc space between the vertebrae.

3. The procedure of claim 1, including energizing the cutting blade by using an ultrasonic driver.

4. The procedure of claim 1, including exposing surfaces of the bone segments formed within each of the adjacent bones to be fused after rotating the cutting blade, whereby the exposed surfaces face one another across the defined space between the bones.

5. The procedure of claim 1, including inserting a cage to a desired position inside the defined space between the adjacent bones.

6. The procedure of claim 5, wherein the desired position is one at which the cage is compressed between the bones.

7. The procedure of claim 5, including configuring the cage to provide a common pivot point about which the cutting blade and the paddle are rotated.

8. The procedure of claim 5, including forming a chamber in the cage that opens at top and bottom ends of the cage, and forming an opening in a side of the cage for allowing passage of a tool shaft including the cutting blade at a distal end of the shaft into the chamber.

9. The procedure of claim 5, including configuring the cage as a fixation device for connecting the adjacent bones to one another.

10. The procedure of claim 8, including forming a port in the cage for injecting a coagulating agent into the chamber in the cage.

11. A procedure for harvesting graft material for use during bone fusion surgery, comprising:
providing a cage having a front wall, a rear wall, and a chamber inside the cage between the front and the rear wall;
arranging a bone cutting mechanism including a generally U-shaped cutting blade and a paddle within the chamber between the front and the rear wall of the cage, the cutting blade having a base, a pair of legs spaced apart a certain width from one another, and a closed end that extends a certain length from the base of the blade, and both of the cutting blade and the paddle are rotatable about a common axis;
inserting the cage to a desired position in a defined space between adjacent bones that are to be fused to one another, and rotating the cutting blade so that the blade cuts into the bones thereby forming a generally semi-circular solid bone segment within each one of the bones, wherein each bone segment has a width corresponding to the spacing between the legs of the cutting blade, and a radius corresponding to the length between the base and the closed end of the cutting blade; and
rotating the paddle to displace the solid bone segments formed within the adjacent bones angularly, whereby a first end portion of each bone segment enters the bone opposite the bone within which the segment was formed, an intermediate portion of the bone segment spans the space between the bones, and a second end portion of the bone segment remains in the bone within which the segment was formed;
each bone segment thereby defining a strut graft for promoting a fusion of the adjacent bones to one another.

12. The procedure of claim 11, including:
supporting an outer shaft to extend along the common axis from the front wall of the cage toward the rear wall, and forming a head on the outer shaft to engage a first mating tool from outside the cage for rotating the outer shaft about the common axis;
supporting a rear end of a sleeve at the rear wall of the cage in axial alignment with the outer shaft;
joining a first leg of the U-shaped bone cutting blade to an end of the outer shaft, and joining a second leg of the cutting blade to a front end of the sleeve;
extending an inner shaft axially inside the outer shaft and the sleeve, and forming a front end of the inner shaft for engaging a second mating tool from outside the cage for rotating the inner shaft about the common axis;
exposing a section of the inner shaft between the end of the outer shaft where the first leg of the cutting blade is joined, and the front end of the sleeve where the second leg of the blade is joined; and
configuring the paddle to extend from the exposed section of the inner shaft.

13. The procedure of claim 11, including activating the bone cutting blade ultrasonically.

14. The procedure of claim 12, including forming the head of the outer shaft as a cylindrical socket.

15. The procedure of claim 11, wherein the adjacent bones to be fused are vertebrae in a patient's spine, and the defined space inside of which the cage is inserted is a disc space between the vertebrae.

* * * * *